US00PP27505P3

(12) United States Plant Patent
Wells

(10) Patent No.: US PP27,505 P3
(45) Date of Patent: Dec. 27, 2016

(54) ***POLYSPORA* PLANT NAMED 'MONSAPARUBY'**

(50) Latin Name: *Polyspora longicarpa*
Varietal Denomination: MonSaPaRuby

(71) Applicant: Richard Wells, Dayton, OR (US)

(72) Inventor: Richard Wells, Dayton, OR (US)

(73) Assignee: Monrovia Nursery Company, Azusa, CA (US)

( * ) Notice: Subject to any disclaimer, the term of this patent is extended or adjusted under 35 U.S.C. 154(b) by 100 days.

(21) Appl. No.: 14/121,842

(22) Filed: Oct. 22, 2014

(65) Prior Publication Data

US 2016/0120085 P1 Apr. 28, 2016

(51) Int. Cl.
*A01H 5/02* (2006.01)

(52) U.S. Cl.
USPC ..... Plt./226

(58) Field of Classification Search
USPC ..... Plt./226
See application file for complete search history.

*Primary Examiner* — June Hwu
(74) *Attorney, Agent, or Firm* — Cassandra Bright

(57) ABSTRACT

A new and distinct *Polyspora* cultivar named 'MonSaPaRuby' is disclosed, characterized by very glossy, dark green leaves with a unique Greyed-Red and Greyed-Orange coloration to the new foliage and stems. Plants have a distinctive upright habit. The new cultivar is a *Polyspora*, suitable for ornamental garden purposes.

3 Drawing Sheets

Latin name of the genus and species: *Polyspora longicarpa.*

Variety denomination: 'MonSaPaRuby'.

BACKGROUND OF THE INVENTION

The new cultivar is a product of a commercial breeding program under the direction of the inventor, Richard Wells. The goal of the breeding program is to identify and select interesting new woody plants with ornamental commercial value. In February 2010, the new variety *Polyspora longicarpa* 'MonSaPaRuby' was selected as a seedling among a group of *Polyspora longicarpa* seedlings grown at a commercial nursery in Dayton, Oreg. The seed parent is an unnamed, unpatented *Polyspora longicarpa* variety, the pollen parent is unidentified.

Plant material of the new variety was first propagated during July of 2011 at a commercial nursery in Dayton, Oreg. Four additional generations have been reproduced since 2011, and have shown that the unique features of this cultivar are stable and reproduced true to type. The first and subsequent propagation method are by semi-hardwood cuttings.

SUMMARY OF THE INVENTION

The cultivar 'MonSaPaRuby' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'MonSaPaRuby' These characteristics in combination distinguish 'MonSaPaRuby' as a new and distinct *Polyspora* cultivar:

1. Very shiny dark green foliage.
2. Prolific flowering

3. Unique rich Greyed-Red to Greyed-Orange coloration of new foliage.
4. The petioles of the new growth Greyed-Red RHS 178A before turning green.
5. Attractive, upright growth habit.

COMPARISON TO PARENT VARIETY

The new variety is similar in most horticultural characteristics to the unnamed *Polyspora longicarpa* parent. The new variety however, differs in the following:

1. Different, more upright plant habit. Glossy darker green foliage.
2. Darker green, glossier mature foliage.
3. New variety has distinctive petiole coloration of Greyed-Red RHS 178A on new growth, before turning green.
4. The new foliage of the 'MonSaPaRuby' is uniquely Brown and Greyed-Orange before turning green.

COMMERCIAL COMPARISON

'MonSaPaRuby' is best compared to the commercial variety *Polyspora longicarpa* Green Leaf, unpatented. Plants of the new cultivar 'MonSaPaRuby' are similar to plants of 'Green Leaf' in most horticultural characteristics, however, plants of the new cultivar 'MonSaPaRuby' differ in the following:

1. Denser plant canopy
2. Darker green, glossier mature foliage.
3. New variety has distinctive petiole coloration of Greyed-Red RHS 178A on new growth, before turning green.
4. The new foliage of the 'MonSaPaRuby' is uniquely Brown and Greyed-Orange before turning green.
5. More upright growth habit.

BRIEF DESCRIPTION OF THE PHOTOGRAPHS

The accompanying photographs illustrate in full color typical characteristics of the new *Polyspora*. The photographs were taken using conventional techniques and although colors may appear different from actual colors due to light reflectance it is as accurate as possible by conventional photographic techniques.

DETAILED BOTANICAL DESCRIPTION

Figure 1:
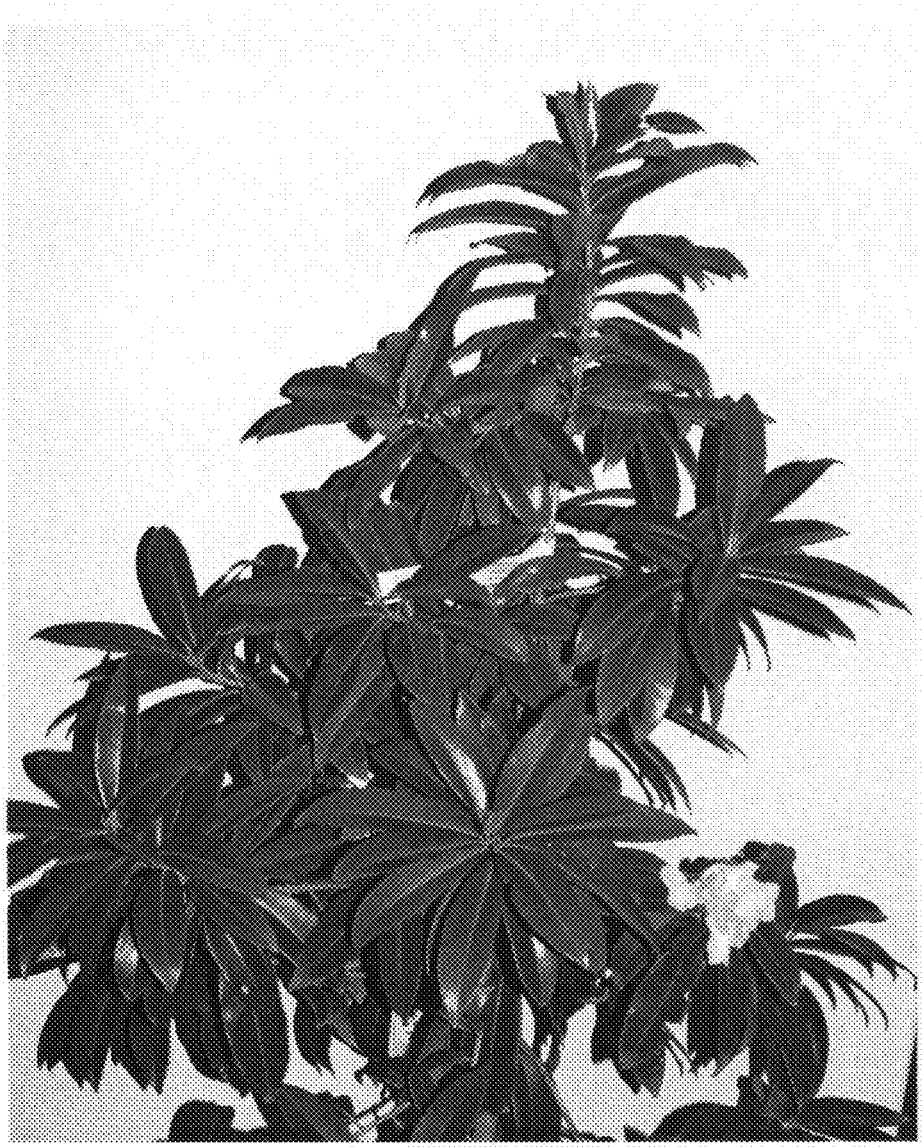
FIG. 1 illustrates in full color a typical plant of 'MonSaPaRuby' grown outdoors in Visalia, Calif. during Fall, with mature, green foliage. This plant is approximately 3 years old, grown in a 7 gallon nursery container.
Figure 2:
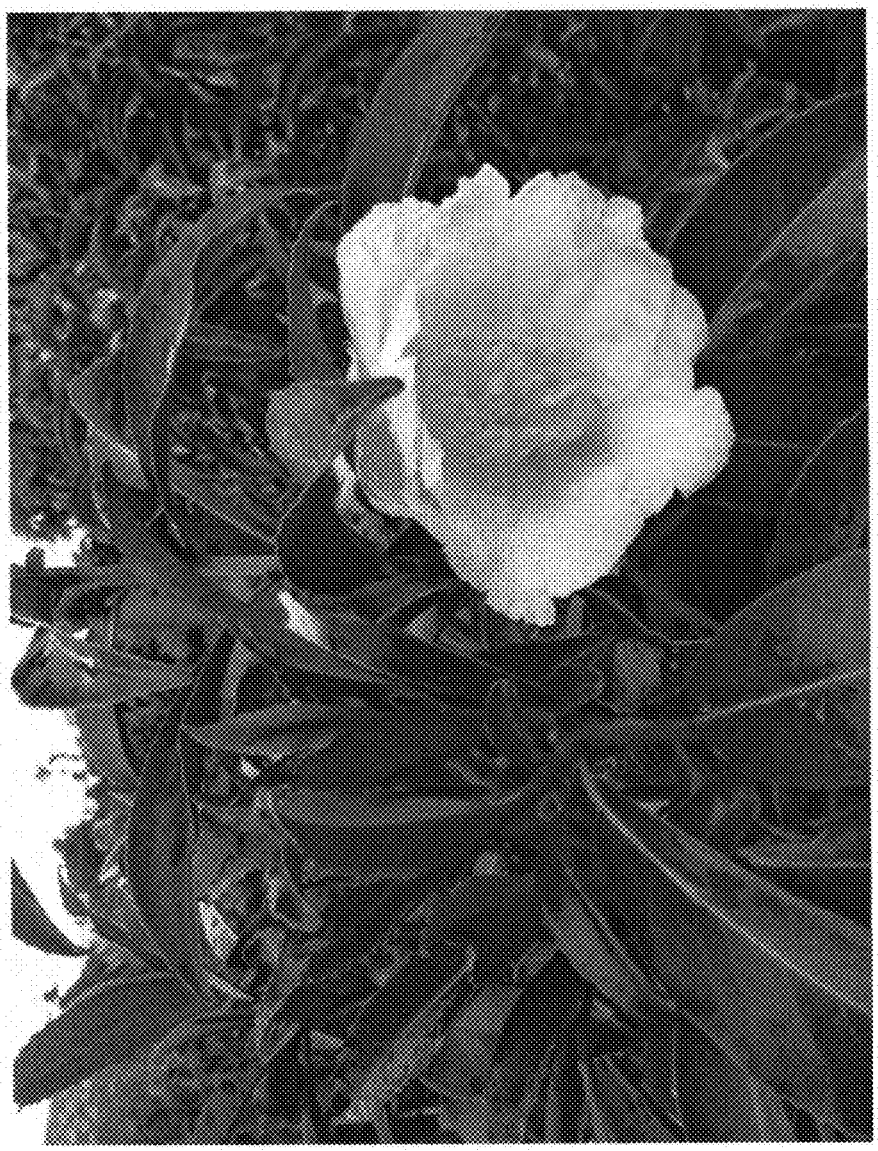
FIG. 2 illustrates in full color a close up of typical immature foliage and an open flower of 'MonSaPaRuby' grown outdoors in Dayton, Oreg. This photograph was taken during the Spring.
Figure 3:
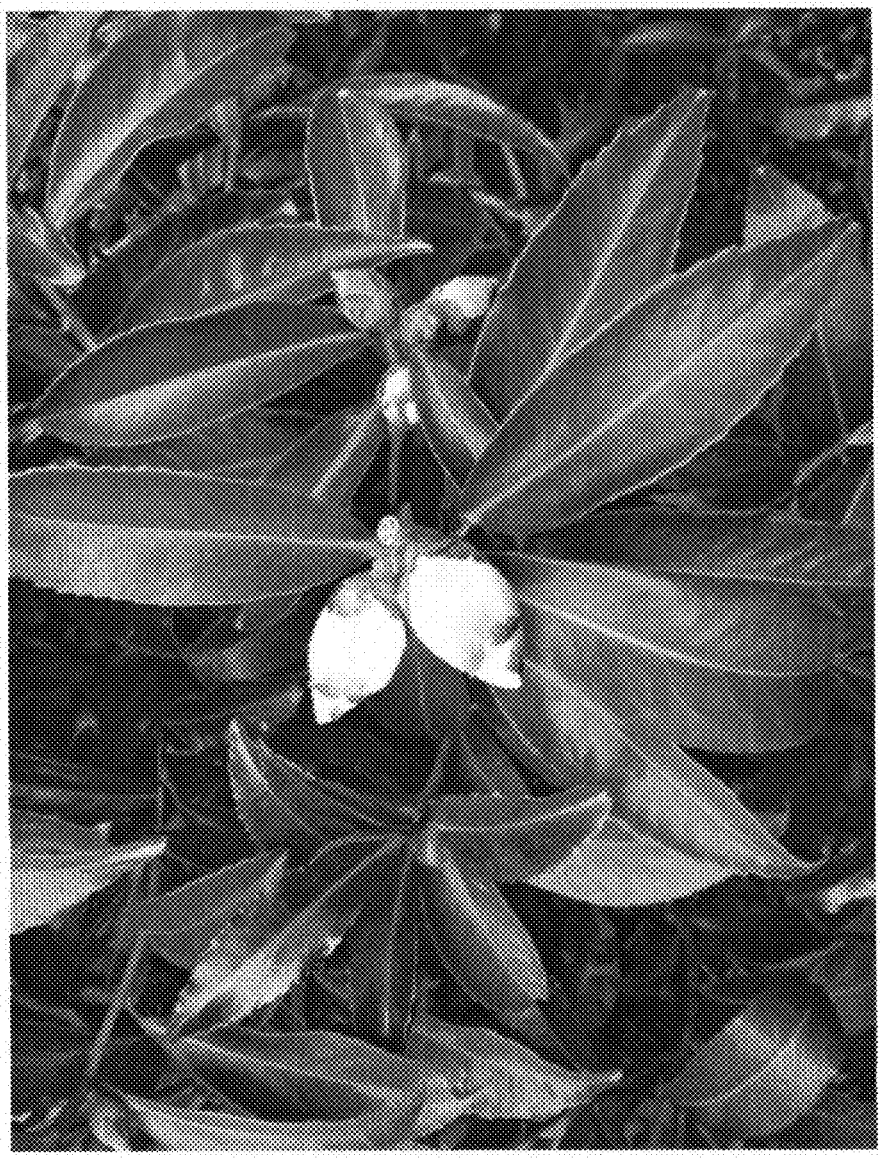
FIG. 3 illustrates in full color a close up of typical immature, foliage and flower buds of 'MonSaPaRuby' grown outdoors in Dayton, Oreg. This photograph was taken during the Spring.

In the following description, color references are made to The Royal Horticultural Society Colour Chart 2007 except where general terms of ordinary dictionary significance are used. The following observations and measurements describe 'MonSaPaRuby' plants grown outdoors in Visalia, Calif. Plants are approximately 3 years old, in a 7 gallon nursery container. Temperatures ranged from approximately 2° C. to 25° C. at night to 5° C. to 38° C. during the day. Measurements and numerical values represent averages of typical plant types.

Botanical classification: *Polyspora longicarpa* 'MonSaPaRuby'.

PROPAGATION

Propagated by semi-hardwood cuttings.

Root description: Woody roots, colored near Brown 200C and 200D.

PLANT

Growth habit: Upright, somewhat pyramidal evergreen woody shrub.
Height: Approximately 125 cm.
Plant spread: Approximately 90 cm.
Branching characteristics: Semi free branching.
Length of lateral branches: Average range 20 to 40 cm.
Diameter of lateral branches: Approximately 0.7 cm.
Number of lateral branches: Approximately 15.
Pinching required: No, un-pinched plant described.
Lateral branch shape: Round.
Lateral branch strength: Strong and flexible.
Lateral branch color:
- *Immature*.—New growth near Greyed-Orange 175C and Greyed-Orange 176A. Greyed-Orange flushing heavier during Spring growth.
- *Mature*.—Near Yellow-Green 144C, becoming near Grey-Brown 199C with more age.

Lateral branch texture:
- *Immature*.—Smooth.
- *Mature*.—Somewhat rough and very slightly scaly.

Number of leaves per lateral branch: Average 27 per 40 cm.
Internode: Very few leaves near center of plant. Towards end of branches, internode range from approximately 1.0 to 2.0 cm.
Age of plant described: Approximately 3 years.

FOLIAGE

Leaf:
- *Arrangement*.—Alternate, single.
- *Average length*.—Approximately 15.8 cm.
- *Average width*.—Approximately 4.8 cm.
- *Shape of blade*.—Elliptic.
- *Apex*.—Acute and retuse.
- *Base*.—Attenuate.
- *Attachment*.—Petiolate.
- *Margin*.—Shallow serrate.
- *Texture of top surface*.—Glabrous.
- *Texture of bottom surface*.—Glabrous.
- *Appearance of top surface*.—Very glossy.
- *Appearance of bottom surface*.—Matte.
- *Color*.—Young foliage upper side: Near RHS Green 137A, flushed(heaviest on Spring new growth) with an overlay closest to Greyed-Red 178A. Young foliage under side: Near RHS Green 137C background coloration, heavily flushed Greyed-Orange 175A. Mid vein colored Greyed-Red 178A. Mature foliage upper side: Near RHS Green 139A. Mature foliage under side: Near RHS Green 138A.
- *Venation*.—Type: Pinnate. Venation color upper side: Near RHS Green 143C. Venation color under side: Near RHS Yellow-Green N144A.
- *Durability of foliage to stresses*.—Strong, leathery foliage does not tear easily.

Petiole:
- *Average length*.—Approximately 0.8 cm.
- *Diameter*.—Approximately 0.35 cm.
- *Texture*.—Glabrous.
- *Color*.—New Growth: Upper Surface: Near RHS Greyed-Red RHS 178A. Lower Surface: Near RHS Greyed-Red RHS 178A. Mature Growth: Upper Surface: Near RHS Green 137C. Lower Surface: Near RHS Yellow-Green 144A.

FLOWER

Bud:
- *Bud shape*.—Tapered ovate.
- *Bud length*.—Approximately 5.3 cm.
- *Bud diameter*.—Approximately 3.5 cm.
- *Bud color*.—Near RHS White 155A, tips near Greyed-Red 178B and 178C.

Bloom period:
- *Natural season*.—Spring through Fall, with heaviest bloom during Spring and early Summer.

Flower:
- *Arrangement*.—Rotate flowers occurring at leaf axils. Typically occurring 1 to 4 at a terminal axil.
- *Height*.—Approximately 4.0 cm.
- *Width*.—Approximately 11.0 cm.
- *Facing direction*.—Outwardly and upwardly facing.
- *Quantity of flowers and buds per branch*.—Average 3 blooms per lateral branch.
- *Rate of opening*.—Individual flowers: Fully open approximately 4 days from the bud stage.
- *Flower longevity on plant*.—Approximately 7 days.
- *Persistent or self-cleaning*.—Self-Cleaning.
- *Fragrance*.—Faint to none.

Petals:
*Quantity*.—Average 8 to 10.
*Length of petal*.—Average 5.5 cm.
*Width of petal*.—Average 4.3 cm.
*Apex*.—Retuse.
*Base*.—Truncate.
*Shape of petal*.—Obovate.
*Petal margin*.—Entire, with some ruffling.
*Petal arrangement*.—Rotate, overlapping.
*Petal appearance*.—Matte, upper and lower surfaces.
*Petal texture*.—Glabrous, upper and lower surfaces.
Color:
*Upper surface at first opening*.—Near RHS White 155A.
*Upper surface at maturity*.—Near RHS White 155C.
*Upper surface at fading*.—Near RHS White 155A.
*Under surface at first opening*.—Near RHS White 155A, base flushed with Yellow-Green 144A.
*Under surface at maturity*.—Near RHS White 155C.
*Under surface at fading*.—Near RHS White 155C.
Bracteoles: Caducous.
*Quantity*.—Average 3 to 7.
*Length*.—Average 1.7 cm.
*Width*.—Average 2.3 cm.
*Shape of*.—Deltoid.
*Color*.—Near RHS Green 138A, margin Greyed-Red 181A. Turning 181A at shedding.
Petaloids: None.

SEPAL

Number: 5.
Sepal appearance: Matte.
Sepal texture: Slightly pubescent outer surface, glabrous inner surface.
Sepal arrangement: Rotate, slightly overlapping.
Sepal length: Approximately 1.5 cm.
Sepal width: Approximately 1.9 cm.
Sepal shape: Flattened oval.
Base: Truncate.
Apex shape: Emarginate.
Margin: Entire.
Color: Near RHS Green 143C, inner and outer surfaces.

PEDUNCLE

Length: Approximately 0.6 cm.
Diameter: Approximately 0.4 cm.
Strength: Very strong.
Texture: Slightly pubescent.
Color: Near RHS Green 143C.

REPRODUCTIVE ORGANS

*Number of pistils per flower*.—1.
*Pistil length*.—Approximately 4.5 cm.
*Stigma shape*.—Capitate.
*Stigma color*.—Near RHS yellow-Green 144C.
*Style color*.—Near RHS Yellow-Green 145C.
*Style length*.—Approximately 3.5 cm.
*Ovary color*.—Near RHS Green-White 157A.
*Stamens quantity*.—Approximately 100 to 120. Stamens adnate to petals.
*Filament length*.—Average 1.9 cm.
*Filament basal texture*.—Slightly sericeous.
*Filament color*.—Near RHS Yellow 10C.
*Anther shape*.—Linear.
*Anther size*.—0.4 cm.
*Anther color*.—Near RHS Yellow-Orange 14B.
*Pollen color*.—Near RHS Yellow-Orange 17B.
*Pollen quantity*.—Scant to Moderate.

OTHER CHARACTERISTICS

Disease and pest resistance: Not observed to be susceptible nor resistant to normal diseases and pests of *Polyspora longicarpa*.
Drought tolerance: No tolerance for drought.
Temperature tolerance: USDA Zone 7 and above.
Fruit/seed production: Not observed to date.

What is claimed is:

1. A new and distinct cultivar of *Polyspora* plant named 'MonSaPaRuby' as herein illustrated and described.

* * * * *